United States Patent [19]

Miltenyi

[11] Patent Number: 5,711,871
[45] Date of Patent: Jan. 27, 1998

[54] MAGNETIC SEPARATION APPARATUS

[75] Inventor: Stefan Miltenyi, Bergisch Gladbach, Germany

[73] Assignee: Miltenyi Biotec GmbH, Bergisch Gladbach, Germany

[21] Appl. No.: 487,277

[22] Filed: Jun. 7, 1995

Related U.S. Application Data

[63] Continuation-in-part of Ser. No. 394,834, Feb. 27, 1995.

[51] Int. Cl.⁶ .................................................... B01D 35/06
[52] U.S. Cl. ..................... 210/86; 210/143; 210/196; 210/222; 210/416.1; 210/420
[58] Field of Search ............................. 210/86, 143, 196, 210/222, 416.1, 418, 419, 420, 427, 223; 436/526

[56] References Cited

U.S. PATENT DOCUMENTS

| | | | |
|---|---|---|---|
| 3,791,930 | 2/1974 | Saxholm . | |
| 3,843,450 | 10/1974 | Saxholm . | |
| 3,968,313 | 7/1976 | Pearlman | 428/450 |
| 3,970,518 | 7/1976 | Giaver | 195/1.5 |
| 3,981,776 | 9/1976 | Saxholm . | |
| 3,985,608 | 10/1976 | Saxholm . | |
| 3,985,646 | 10/1976 | Oder . | |
| 4,018,886 | 4/1977 | Giaver | 424/12 |
| 4,021,308 | 5/1977 | Saxholm . | |
| 4,054,513 | 10/1977 | Windle . | |
| 4,140,582 | 2/1979 | Saxholm . | |
| 4,169,804 | 10/1979 | Yapel . | |
| 4,213,825 | 7/1980 | Saxholm . | |
| 4,219,411 | 8/1980 | Yen et al. . | |
| 4,230,685 | 10/1980 | Senyei et al. | 424/12 |
| 4,324,859 | 4/1982 | Saxholm . | |
| 4,371,624 | 2/1983 | Saxholm . | |
| 4,375,407 | 3/1983 | Kronick | 209/8 |
| 4,452,773 | 6/1984 | Molday | 424/1.1 |
| 4,526,681 | 7/1985 | Friedlaender et al. . | |
| 4,554,088 | 11/1985 | Whitehead et al. | 252/62.54 |
| 4,557,979 | 12/1985 | Higginbottom et al. | 428/460 |
| 4,591,556 | 5/1986 | Saxholm . | |
| 4,657,868 | 4/1987 | Saxholm . | |
| 4,664,796 | 5/1987 | Graham et al. | 210/222 |
| 4,710,472 | 12/1987 | Saur et al. . | |
| 4,738,773 | 4/1988 | Muller-Ruchholtz et al. | 209/214 |
| 4,770,183 | 9/1988 | Groman et al. | 128/654 |

(List continued on next page.)

FOREIGN PATENT DOCUMENTS

| | | |
|---|---|---|
| 452342-B | 11/1994 | Germany . |
| 8701607 | 3/1987 | WIPO . |

OTHER PUBLICATIONS

Molday, et al., *Nature* (1977) 268:437–438.
Kronick, et al., *Science* (1978) 200:1074–1076.
Widder, et al., *J. Pharm. Sci.* (1979) 68:79–82.
Molday, et al., *FEBS Letters* (1984) 170(2):232–238.
Molday, et al., *J. Immunol. Meth.* (1982) vol. 52:353–367.
Sato et al. (1986) *J. of Biochem.* vol. 100, No. 6, pp. 1481–1492.
de Latour et al. (1983) *IEEE Transactions on Magnetics*, vol. MAG–19, pp. 2127–2129.

*Primary Examiner*—Matthew O. Savage
*Attorney, Agent, or Firm*—Cooley Godward LLP

[57] ABSTRACT

Improved magnetic separation devices for magnetic separation procedures are provided. The improved separation devices contain matrices which provide uniform pores or channels that reduce the entrapment of air or non-target substances, and decrease the loss of target substances due to mechanical disruption. Target cells, from various systems and organs, or other target biological substances are labeled in conjunction with a suitable specific binding member, and isolated using the devices and methods of the present invention. In its simplest form, the cell separation system of the present invention has two main components: a magnetic separator and a cell separation reagent. A more complex separation device includes fluid passages, collection and storage containers and the separation column. The fluid circuitry can be constructed with integrated valves, or the valves may be applied externally to the fluid pathways.

8 Claims, 4 Drawing Sheets

U.S. PATENT DOCUMENTS

| | | |
|---|---|---|
| 4,795,698 | 1/1989 | Owen et al. . |
| 4,859,319 | 8/1989 | Borsari .................................... 210/86 |
| 4,992,377 | 2/1991 | Saxholm . |
| 5,137,629 | 8/1992 | Dauchez . |
| 5,200,084 | 4/1993 | Liberti et al. . |
| 5,240,856 | 8/1993 | Goffe et al. . |
| 5,385,707 | 1/1995 | Miltenyi et al. . |
| 5,411,863 | 5/1995 | Miltenyi . |
| 5,536,475 | 7/1996 | Moubayed et al. .................. 436/526 |

MAGNETIC SEPARATION APPARATUS

CROSS REFERENCE TO RELATED APPLICATIONS

This application is a continuation-in-part of U.S. patent application Ser. No. 08/394,834, filed Feb. 27, 1995 still pending.

TECHNICAL FIELD

The field of this invention is the application of high gradient magnetic separation (HGMS) to the separation of biological materials.

BACKGROUND

Magnetic separation is a procedure for selectively retaining magnetic materials in a chamber or column disposed in a magnetic field. A target substance, including biological materials, may be magnetically labeled by attachment to a magnetic particle by means of a specific binding partner which is conjugated to the particle. A suspension of the labeled target substance is then applied to the chamber. The target substance is retained in the chamber in the presence of a magnetic field. The retained target substance can then be eluted by changing the strength of, or by eliminating, the magnetic field.

A matrix of material of suitable magnetic susceptibility may be placed in the chamber, such that when a magnetic field is applied to the chamber a high magnetic field gradient is locally induced close to the surface of the matrix. This permits the retention of weakly magnetized particles, and the approach is referred to as "high gradient magnetic separation" (HGMS).

Previously known or commercially available high gradient magnetic separators generally contain a steel wool or wire matrix. Such matrices often give rise to non-specific binding or entrapment of biological substances or sample components other than the target substance. In addition, such matrices may have non-uniform pores or pathways through which the sample passes, which result in variable separation results. Such non-uniform matrices may also produce magnetic gradients and inconsistent flow patterns that result in the variability of separation results.

The use of HGMS in biological separations requires that the conditions provide a high yield with substantial purity. Accordingly, it would be desirable to provide high gradient magnetic separators, devices and methods that are relatively easy to construct and use, yet provide maximized and uniform magnetic field gradients and flow characteristics during use. It would be most advantageous if such magnetic separators, devices and methods could be used to perform a variety of cell sorting or assay procedures with the selection of the appropriate specific binding member by which the target substance will be magnetically labeled.

Relevant Literature

Magnetic separation techniques have been known for many years. The techniques have been used to separate ferrous metal particles from a fluid such as lubricating oil or aqueous slurries of clay, as described in Oder, U.S. Pat. No. 3,985,646. In some cases, high gradient magnetic separation was used, for example Windle, U.S. Pat. No. 4,054,513; Dauchez, U.S. Pat. No. 5,137,629; and Friedlaender et al., U.S. Pat. No. 4,526,681. In high gradient magnetic separation, a separation chamber containing a magnetizable matrix made of materials such as steel wool, metal-coated fibers, and metal tacks, bars, plates, fillings, wires or ball bearings, is subjected to a magnetic field. When the magnetic field is applied, any metal particles in the fluid are attracted to the matrix. To remove the metal particles from the matrix, the magnetic field is turned off or removed, and the chamber is flushed.

Developments in biological and diagnostic systems have combined magnetic separation techniques with the use of binding members, such as antibodies, having a specific affinity for a material of interest that is to be separated or isolated from a mixture of materials (Yapel, U.S. Pat. No. 4,159,804; Yen et al., U.S. Pat. No. 4,219,411; Saur et al., U.S. Pat. No. 4,710,472; Owen et al. U.S. Pat. No. 4,795, 698; Liberti et al. U.S. Pat. No. 5,200,084). Molday, U.S. Pat. No. 4,452,773 describes the preparation of magnetic iron-dextran microspheres and provides a summary describing the various means of preparation of particles suitable for attachment to biological materials. A description of polymeric coatings for magnetic particles used in HGMS are found in DE 3720844 (Miltenyi) and Miltenyi et al., U.S. Pat. No. 5,385,707. Methods to prepare superparamagnetic particles are described in U.S. Pat. No. 4,770,183.

The use of HGMS with biological systems is of interest in the development of diagnostics. In addition, the identification of antibodies specific for many cell surface antigens has lead to an interest in the development of therapeutic methods involving the selection and transplantation of identifiable cells.

A description of a non-magnetic separator may be found in U.S. Pat. No. 5,240,855 (Goffe et al.).

SUMMARY OF THE INVENTION

The invention provides improvements in high gradient magnetic separation devices, apparatus and methods for the separation of biological materials. The subject devices, apparatus and methods allows a greater specificity and efficiency in the isolation of particular cells, proteins, polysaccharides, and other biological materials, or other materials that are magnetic or are capable of a specific binding interaction with a magnetically labeled binding member.

A magnetic separation column is provided, having a nonmagnetic housing that defines a separation chamber, and a fluid permeable matrix of metallic spheres within the chamber. The spheres form a closely stacked lattice, which creates substantially uniform channels for homogeneous flow during separations. A magnetic separator device may use the separation column in conjunction with a prefilter device. The device may be used in an instrument having a permanent or electromagnet for use during separations, with an optional retractable arm for moving the magnet, pumping means for washing and separating the target material, and a microprocessor for controlling the separation fluid flow.

DESCRIPTION OF THE SPECIFIC EMBODIMENTS

Improved magnetic separators, devices and methods for magnetic separation procedures are provided. The improved matrices of the magnetic separators provide uniform pores or channels that reduce the entrapment of air or non-target substances, decrease the loss of target substances due to mechanical disruption, and have substantially homogeneous flow characteristics. The retention of magnetically labeled material is dependent on the interaction of flow forces and magnetic attraction, therefore a more homogeneous flow improves the separation efficiency.

Biological substances, such as target cells from various systems and organs, are magnetically labeled with a suitable specific binding member, and isolated using the devices and methods of the present invention. The isolation of multipotential cells such as hematopoietic stem or progenitor cells are of particular interest. While hematopoietic cell separation is used herein to provide examples of cell separation procedures, the present invention may be applied to a wide range of cell types or other biological substances.

The magnetic separation system of the present invention can be used to magnetically label and isolate any desired target substance. Of particular interest is the separation of a specific component from a complex mixture. The separation system of the present invention has great versatility, in that almost any target substance may be separated once a specific binding member is available. The target substance or analyte may be any member of a specific binding pair, or a substance associated with a member of a specific binding pair. As an example, a cell surface antigen-antibody binding pair may be used to isolate the antigen itself, cells that express the antigen, a particular organelle involved in processing of the antigen, etc. The devices and methods of the present invention are also advantageously applied to diagnostic techniques involving the binding of a receptor and ligand, such as immunoassays, and the like.

In its simplest form, the cell separation system of the present invention has two main components: a magnetic separator and a cell separation reagent. A schematic diagram of a magnetic separator device is given in FIG. 1. The diagram shows the general construction of the separator and the uniform fluid passage that results from the use of a matrix of metallic spheres. FIG. 2 depicts a more complex separation device, including the general positions of fluid passages, collection and storage containers and the separation column. The fluid circuitry can be constructed with integrated valves, or the valves may be applied externally to the fluid pathways.

Figure 2:
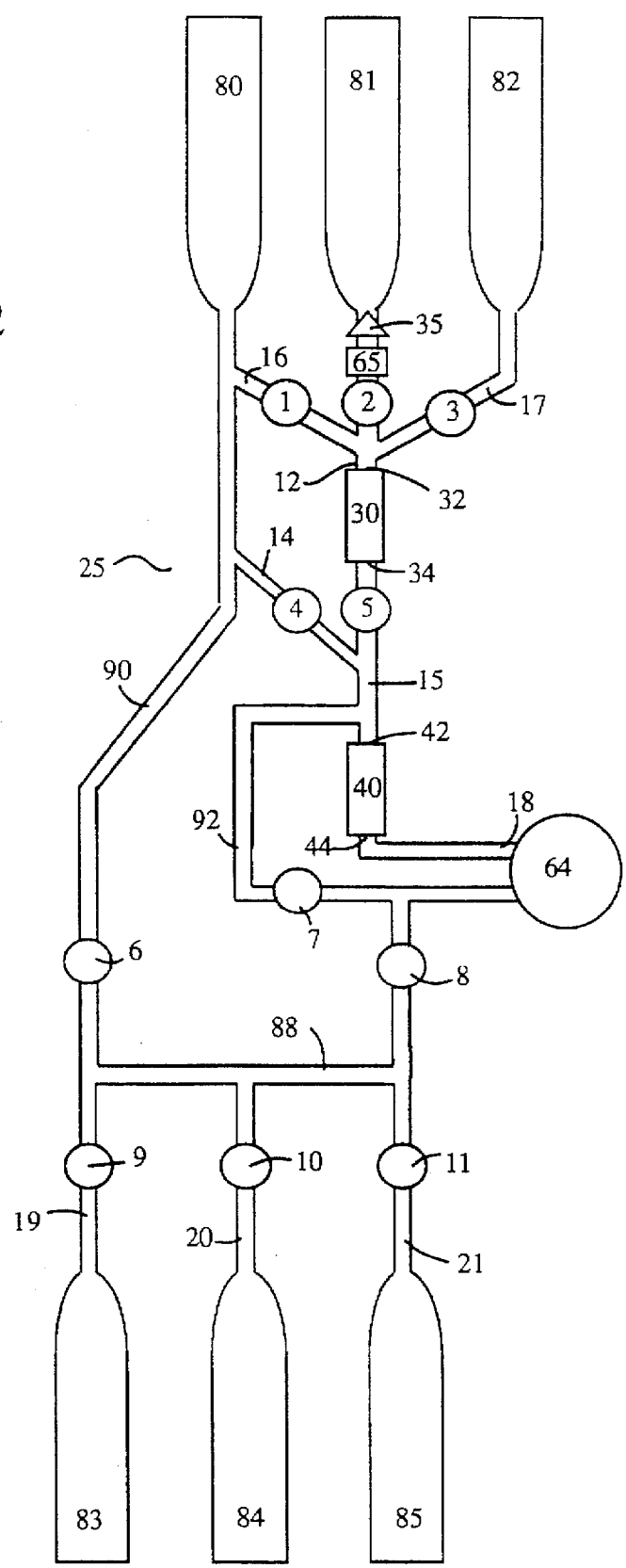
FIG. 2 depicts separation and prefiltration columns, together with the sample and collection containers, interconnected by a series of fluid pathways or fluid circuits. The figure also shows the positioning of valves and a peristaltic pump that is used in the preferred embodiment of the separation system.
Figure 3:
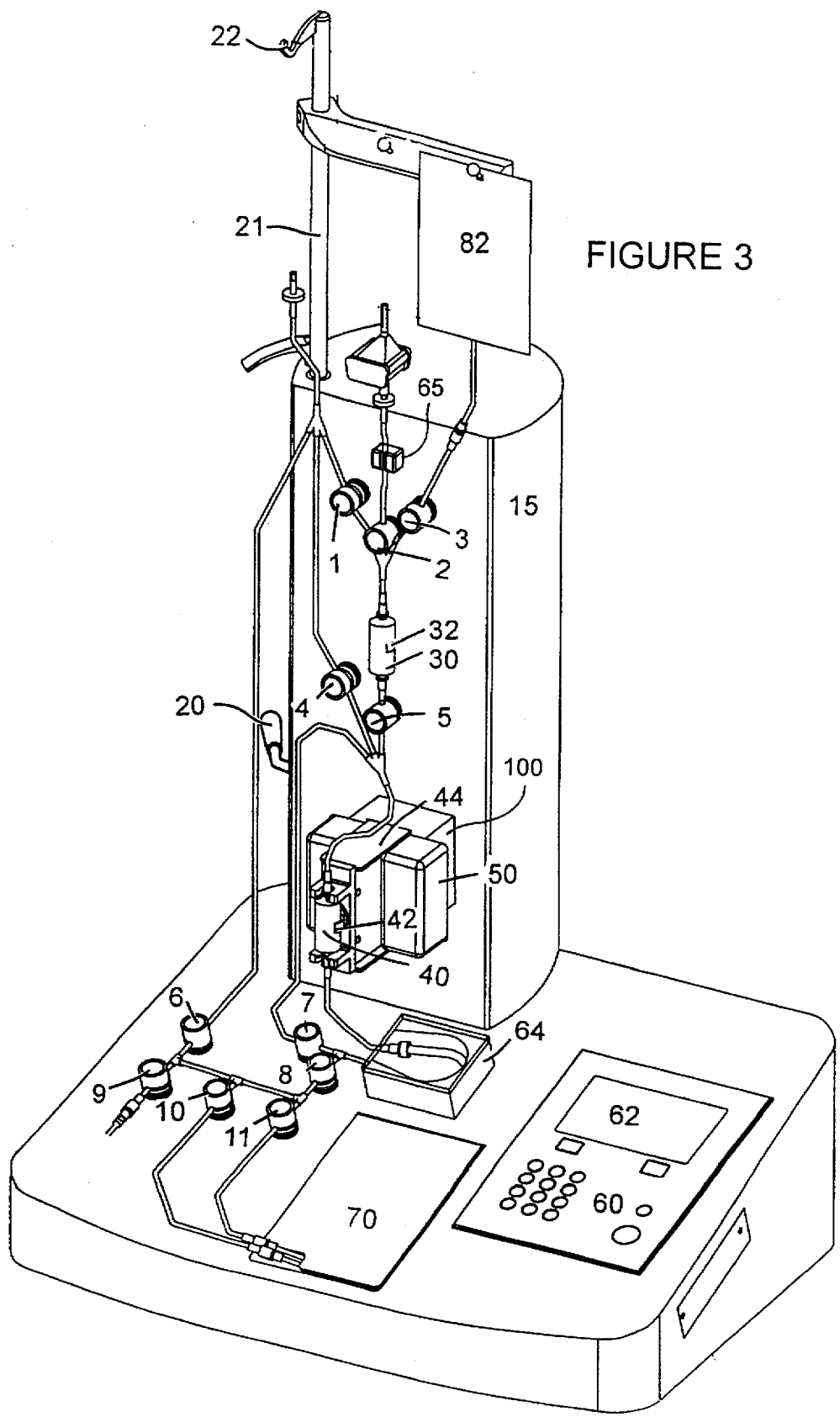
FIG. 3 depicts a computer-controlled unit on which sterile columns, disposable tubing and storage and collection containers, as illustrated in FIG. 2, are appended. In a preferred embodiment, the computer-controlled unit contains a magnet, valves and peristaltic pump.

An optional third component to the preferred cell separation system is a cell separation instrument. FIG. 3 depicts a cell separation instrument, preferably computer-controlled, which may incorporate the valves together with a magnet, pump and keyboard control. A device similar to that of FIG. 2, constructed without valves, may be mounted directly onto the instrument of FIG. 3 for use in the automated separation of target cells.

The cell separation reagent, which may also be referred to as a conjugate, antibody/magnetic particle reagent or magnetic label, includes a magnetically responsive material bound to a specific binding member. There are many well known magnetically responsive materials used in magnetic separation methods. The present invention involves the use of magnetically responsive particles or microparticles. Suitable magnetic particles are described in Molday U.S. Pat. No. 4,452,773 and European Patent Specification 452342-B (published Nov. 20, 1994), which are hereby incorporated by reference. Colloidal sized particles, such as those described in Owen U.S. Pat. No. 4,795,698 and Liberti et al. U.S. Pat. No. 5,200,084, hereby incorporated by reference, are also suitable.

The term "specific binding member" as used herein refers to a member of a specific binding pair, i.e. two molecules, usually two different molecules, where one of the molecules through chemical or physical means specifically binds to the other molecule. The complementary members of a specific binding pair are sometimes referred to as a ligand and receptor. In addition to antigen and antibody specific binding pairs, peptide-MHC antigen and T cell receptor pairs; alternative specific binding pairs of interest include biotin and avidin or streptavidin; carbohydrates and lectins; complementary nucleotide sequences (including nucleic acid sequences used as probes and capture agents in DNA hybridization assays); peptide ligands and receptor; effector and receptor molecules; hormones and hormone binding protein; enzyme cofactors and enzymes; enzyme inhibitors and enzymes; secretion markers, as described in International application PCT/US93/10126; autologous monoclonal antibodies, and the like. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc. so long as an epitope is present.

Immunological specific binding pairs include antigens and antigen specific antibodies or T cell antigen receptors. Suitable antigens may be haptens, proteins, peptides, carbohydrates, etc. Recombinant DNA methods or peptide synthesis may be used to produce chimeric, truncated, or single chain analogs of either member of the binding pair, where chimeric proteins may provide mixture(s) or fragment (s) thereof, or a mixture of an antibody and other specific binding members. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

For brevity, the separation system will mainly be described in terms of its ability to specifically select and separate a defined population of cells (target cells) from a mixed cell population, such as peripheral blood, bone marrow, blood from the umbilical cord or placenta, fetal blood or a leukapheresis product. It will also be appreciated that some tissues may be disrupted into a single cell or monodisperse suspension to allow isolation of a particular cell subset, such as the separation of tumor infiltrating lymphocytes from a tumor mass, the separation of islet cells from kidney tissue, etc. For example, different cell types may be labeled with a specific antibody to allow cell purging and/or cell enrichment. The target cell population is generally identified by a specific binding member, as described above, which selectively binds to a cell surface antigen present on the target cells. It should be understood, however, that the subject apparatus and method is not limited to such uses.

For simplicity, the specific binding member will be exemplified herein by an antibody. The antibody may be directly or indirectly bound to a magnetic particle. If the antibody is directly bound to the magnetic particle, then the target cell population is magnetically labeled when the antibody binds to the cell surface antigen. If the antibody is indirectly bound to the magnetic particle, then the target cell population is susceptible to magnetic labeling when the antibody is bound to the target cells. The antibody-bound cell population is actually labeled by further contacting the cells with a specific binding member for the antibody, where that specific binding member is itself bound to a magnetic particle. The target cells, identified by such magnetic labeling, are then separated from other cells by means of a magnetic field. For example, a specific binding member such as avidin can be conjugated to a magnetic particle where the avidin binds to a biotinylated antibody that in turn specifically binds to the target cells.

The specific binding member may be directly attached to the magnetic particle. This may be accomplished by means of reactive groups on the specific binding member and magnetic particle themselves. Alternatively, the specific binding member and magnetic particle may be joined by means of a coupling agent or linker. The terms "coupling agent" or "linker", as used herein, include various bifunctional crosslinking or coupling agents, i.e. molecules containing two reactive groups or "ends", which may be separated by a spacer.

Conventional high gradient magnetic separation matrices are typically prepared from materials such as wires, metal-coated fiber or steel wool. In the improved magnetic separation device of the present invention, the gradient-intensifying matrix of the high gradient magnetic separator is formed from small spheres of magnetically susceptible or ferromagnetic material. Such materials include, but are not limited to iron, steel, cobalt nickel, and other ferromagnetic rare earth metals or alloys thereof. For example, the matrix material may include ferromagnetic metal spheres such as iron spheres (e.g. MARABU Balls, Kugelfabrik Schulte & Co., Wermelskirchen, Germany). Many different methods of manufacturing spheres are known. Usually the spheres have an average diameter ranging from about 0.2 to 1.5 mm for the separation of large cells or cell complexes, and about 0.05 to 0.2 mm diameter for subcellular material. Preferably, the spheres have an average diameter ranging from about 0.2 to 0.5 mm, and most preferably, the spheres are selected to have an average diameter ranging from about 0.2 to 0.3 mm. It is desirable that the size of spheres be relatively homogeneous, usually varying not more than about 15% from the average size, more usually by not more than about 10%, and preferably by not more than about 5%.

Figure 4:
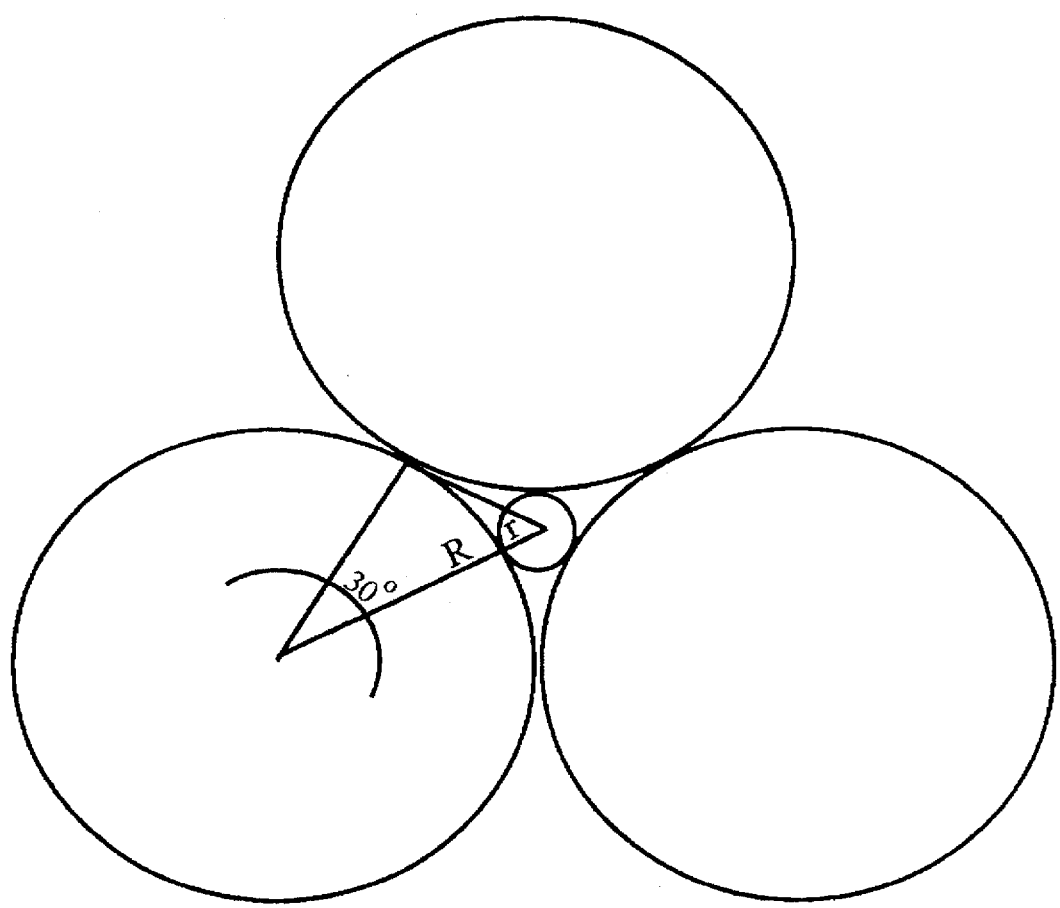
FIG. 4 depicts the flow channel formed between three connecting spheres.

The substantially symmetrical spherical shape and substantially uniform size of the spheres are desirable for the construction of a magnetic separator matrix, as the spheres can assume a lattice configuration wherein the gaps between the spheres form regular channels or pores in the matrix. The lattice configuration is a patterned framework of spheres that forms channels of regular size between adjacent spheres and throughout the matrix. Upon the application of a magnetic field to the separator, magnetic field gradients are created in the gaps between the spheres. The uniform size, and therefore spacing, of the spheres provides for a substantially uniform magnetic gradient throughout the matrix, and substantially uniform fluid flow characteristics. A flow channel is depicted in FIG. 4. The dimensions of the channel can be described by the maximum size bah or particle that would fit between the matrix spheres. With reference to FIG. 4, the geometrical relationship is $r=\sim 0.155$ R. It will be appreciated from the teachings of the present invention that the channel size may be adjusted to an average diameter optimal for the desired separation process by varying the size of the spheres that are used to form the matrix.

The spherical shape provides for the formation of a substantially stable matrix structure when the spheres are packed within a housing that defines a separation chamber. As described in detail below, the matrix is also coated with a substantially fluid impermeable material such as a plastic polymer. On application of a plastic polymer coating, the tight gaps between the spheres are closed, resulting in a hydrodynamically optimized matrix. The resulting ferromagnetic matrix will usually occupy about 60 to 75% of the total volume of the separation chamber, and will be permeable to fluids. The impermeable coating will occupy about 1 to 5% of the total volume. The free volume will range from about 20 to 40% of the total separation chamber volume. In a preferred embodiment, the total matrix will occupy about 75–80% of the total volume of the separation chamber.

Figure 1:
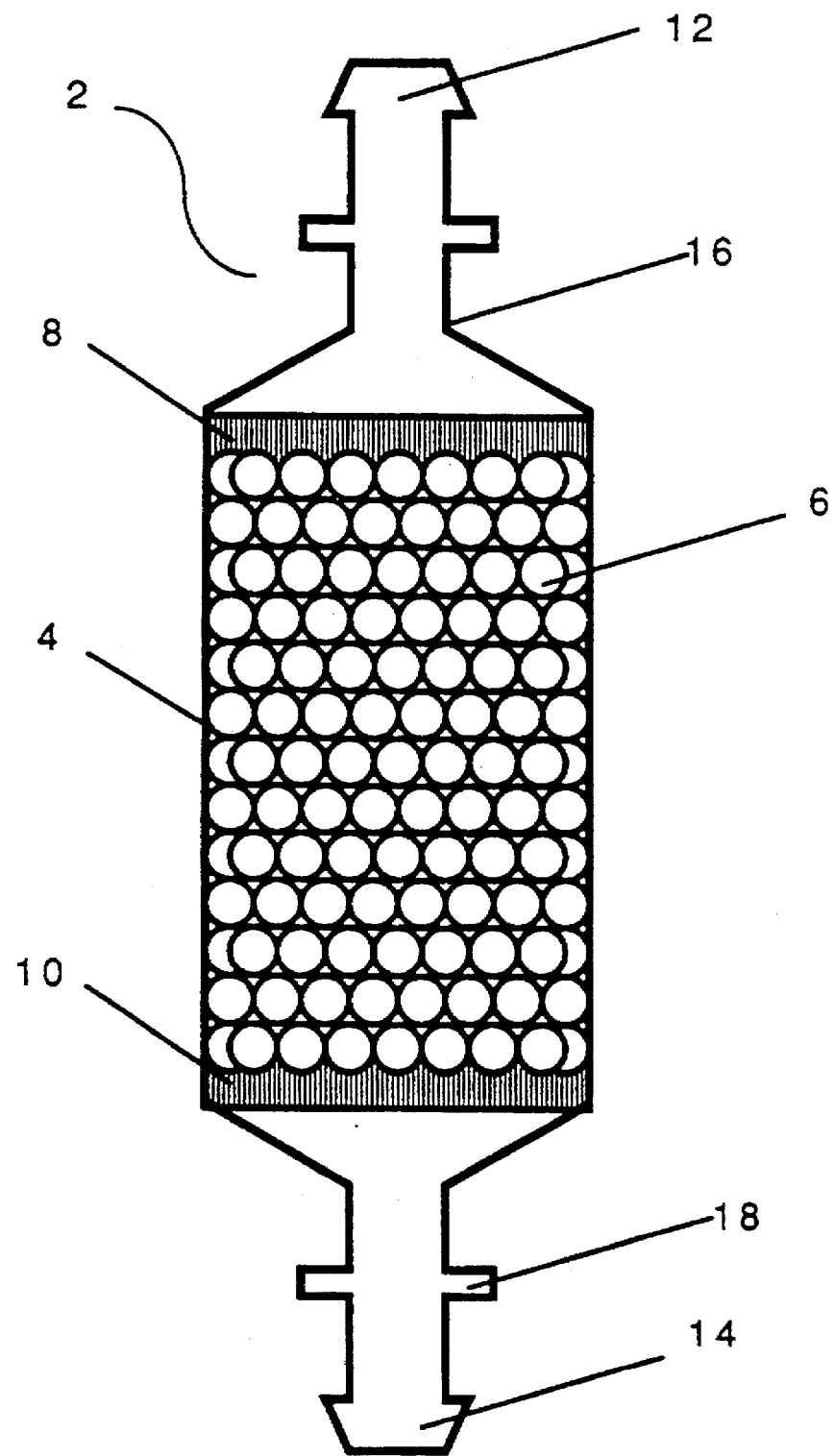
FIG. 1 is a schematic diagram of an exemplary separation or prefiltration column of the present invention.

FIG. 1 presents a schematic of an exemplary separation column. The spheres are not depicted at scale, but so as to better depict the formation of a three dimensional fluid permeable matrix 6. The spheres are packed in a housing 4 which is made of a non-magnetic material. The magnetic separator housing serves as the body of the separation column, and the interior of the housing defines a separation chamber. Housings of various lengths, shapes and diameters are advantageously made of plastic. Suitable nonmagnetic materials for the construction of a magnetic separator housing include stainless steel, glass, plastic, etc.

In one preferred embodiment, the magnetic separator housing is a plastic that the matrix coating will adhere to, allowing improved hydrodynamic properties at the boundary of the matrix and housing. It will be appreciated that the coating material and housing material will be selected for compatibility with one another, e.g. a lacquer coating must be selected that will not result in non-adherent plastic debris accumulating in the column. Various mechanisms are known by which materials adhere to each other, and may be exploited for this purpose. Conveniently, the selection for compatibility may be made based on the solvent used in conjunction with the lacquer. The solvent will be slightly reactive with the plastic housing, such that the lacquer in the solvent will adhere, but not so reactive that the structural integrity of the column is compromised during the lacquer curing process. For example, the coating material may be selected to include a solvent that causes a slight dissolution of the interior of the plastic housing. Upon curing, the plastic rehardens thereby bonding or sealing the coating material and housing material to each other. One of skill in the art will appreciate that information regarding such reactivity is generally available. Exemplary of a suitable solvent and housing combination is methylethylketone and the plastic ULTEM® (General Electric).

Preferably, each of the materials selected for the construction of separation column 2 will also be compatible with sterilization procedures. Preferably, the housing is cylindrical in shape to facilitate the flow of sample through the separation chamber as well as the formation of three dimensional matrix 6 within the housing. The walls of the housing preferably have a thickness of about 1 to 3 mm. The separation column has inlet 12 and outlet 14 ports for the introduction and discharge of fluids. Generally, the inlet and outlet ports are narrow structures relative to the main body of the housing. This facilitates the attachment of the separator to further fluid circuitry in a separation system and advantageously maintains the device as a closed system. The inlet and outlet ports may be positioned at different sites than as depicted in FIG. 1, but it will be appreciated that the overall structure of the separator will preferably provide a separation chamber having the fewest bends or corners which might otherwise slow fluid flow or create spaces where sample might accumulate.

At the inlet and outlet of the column, the column is constructed to have a feeding mechanism ensuring optimal homogeneous distribution and flow through the matrix. The distribution mechanism is comprised of the volume in front of cap layer 8 and the cap layer itself, which serves as a flow resistor. The distribution volume (in milliliters) may be defined relative to the width of the column (in millimeters), usually having a ratio of about 0.1 to 10. The chamber volume in front of base layer 10, as well as the base layer itself, also serves as feeding mechanism for fluids passing into the chamber via the outlet port.

It is preferable to have column dimensions where the diameter to length ratio is at least 0.2 to 1. The actual dimensions of the column will depend on the material being separated, and the desired flow rate for separation. The column dimensions will provide a chamber that will accept a matrix having an adequate surface area to create sufficient magnetic field gradients in the separation chamber and permitting efficient retention of magnetically labeled material. The volume necessary for a given separation may be empirically determined, and will vary with the size, antigen density on the cell surface, antibody affinity, etc. As an example, a sectional area of 3 cm$^2$ allows a flow rate of 5 to 40 ml/minute. The binding capacity of a 2×4 cm matrix is approximately 10$^9$ labeled cells.

To facilitate the manufacture of the separation column, base layer 10 of nonmagnetic porous material is positioned in the housing such that when the ferromagnetic spheres are placed in the chamber they do not pass through outlet port 14. Suitable porous materials for the formation of the base layer include, but are not limited to, porous plastic, sintered metals or glass, grids, etc. For example, various porous frits available from Porex Singwitz, Germany, may be used. Usually, the porous material will have a pore size of about 20 to 200 µm, preferably 50 to 150 µm. A suitable pore size will be selected according to the dimensions of the target substance and the make up of the sample material. In addition, the pore size will not be so large as to allow the spheres to fill the porous openings of the layer material. Following the insertion of the spheres into the chamber, the housing may be shaken or vibrated to facilitate the settling of the spheres into a more uniform configuration. Optionally, cap layer 8 of nonmagnetic porous material is positioned in the housing over the matrix to maintain the uniform configuration of the matrix during storage, handling and use. Pressure may also be applied to cap layer 8 to more firmly pack the spheres within the chamber. Upper portion 16 of the separation column, which includes inlet port 12 in this embodiment, is then positioned on the top of housing 4 and is attached to the housing. For example, when using plastic materials, upper portion 16 might be glued or ultrasonically welded to housing 4 to complete the formation of the separation column. Following the completion of the housing, the matrix is coated.

With reference to FIG. 1, a coating is applied to the fluid permeable matrix described above. The coating is selected to be substantially impermeable to ions, and therefore protects the metallic matrix material from corrosion as well as inhibiting the escape of cations from the matrix, which might damage the cells. In addition to the formation of an impermeable protective layer over the matrix material, a complete coating of the matrix closes the gaps between spheres, providing both mechanical stability to the matrix, and a hydrodynamically optimized matrix. Such mechanical stability is particularly advantageous when the matrix is formed from small spheres of magnetically susceptible or responsive metal, as described above. A coating material, such as a lacquer coating, may be flowed into inlet port 12 of the separation column. The lacquer flows through cap layer 8, matrix 6 and base layer 10, thereby coating the porous surfaces of each component. Excess lacquer is allowed to pass from the chamber through outlet port 14. The coated separation column may be centrifuged to further expel excess coating material from the chamber. The coating is then allowed to dry. The separation column may be heated to further promote the drying of the coating. For example, the coated separation column may be placed in an oven at 110° C. for four to five hours, followed by continued drying at room temperature for three to seven days.

Upon drying, the coating hardens, thereby providing mechanical support to the matrix. Not only does this mechanical support aid in maintaining the integrity of the matrix during the storage and handling of the separation column, it also provides the matrix with a rigid structure which does not exhibit significant elasticity. This rigidity is advantageous because the matrix might otherwise be deformed upon the application of an external magnetic field to the separation column. The applied magnetic field strength of the external magnetic means is typically within a range of about 0.1 to about 1.5 Tesla, and more preferably between about 0.2 to about 0.8 Tesla. The field strength should be great enough and the distance between the magnet and the separation column should be small enough to induce intensified magnetic field gradients within the matrix. To maintain uniform magnetic gradients in the separator, the matrix material should not move or shift in the chamber upon the application of the magnetic field. The spherical metallic components, the housing and the coating are advantageously combined in the present invention to provide an improved matrix with sufficient rigidity to resist substantial deformation when the separation column is placed within a magnetic field.

It is preferable to coat the matrix while the spherical metallic components are within the separation column housing. Coating the matrix within the housing avoids disrupting the matrix after the coating has been applied. Moreover, coating the matrix within the housing serves to fill or seal small void spaces, interstices or crevices formed near the contact points between the spheres, as well as between the spheres and housing, while simultaneously providing a uniform surface to the channels or pores formed by the separated points of the spheres. These channels or pores result in the permeability of the matrix. By sealing the void spaces, there is a decrease in the areas where cells or other solid components of the sample might wedge or become physically entrapped, even in the absence of a magnetic field.

In the completed separation column, the selection of matrix and coating materials will preferably result in channels or pathways through the permeable matrix having an average diameter ranging from 20 to 60 µm and an occupying volume of about 60% to 80% of the total volume of the separation chamber. For example, a separation column for the separation of blood cells may have a final coated-channel size averaging 20 µm, with the matrix occupying approximately 80% of the total volume of the chamber.

Following the preparation of the substantially impermeable coating, the matrix and other interior surfaces of the separation chamber are preferably further treated by the addition of a hydrophilic material such as polyvidone (BASF, Ludwigshafen, Germany). Other suitable hydrophilic coating materials include, but are not limited to, polyvinylpyrrolidine, polyethylene glycol, hydroxyethyl starch, and other hydrophilic coatings, such as acrylamides, surfactants or detergent-type wetting agents, and biological material including, but not limited to, heparin and human serum albumin. The interior surface of the separation chamber may also be made hydrophilic by plasma or corona etching of the surface. The hydrophilic coating provides the interior of the separation column and the fluid permeable matrix with a readily wettable surface. By enhancing the wettability of these surfaces, the introduction of fluid into the separation column will produce a uniform fluid front as it passes through the chamber. This in turn facilitates the removal of air bubbles from the permeable matrix and other void spaces in the separation chamber. It is desirable to maintain the separation column and other device components as a closed system substantially free of air during the separation process. The presence of air in the system during the separation of target cells affects the interior surface tensions and unventilated areas, which can lead to cell destruction.

Referring to FIG. 2, which depicts an improved separation device, separation column 40 may be preceded by a prefiltration device. The figure depicts the prefiltration device as a column 30, however it will be understood that other configurations, such as prefilter, may find use. The prefiltration column is generally a three dimensional structure that may be substantially identical to the separation column in terms of its structural composition. The prefiltration column, however, may have different dimensions, the matrix may be made of spheres having a different composition; e.g. a non-ferromagnetic material, or the matrix may be made of spheres having a different diameter from those used in the separation column, thereby providing a pore or channel size different from that found in the separation column. In one embodiment, the prefiltration column is identical to the separation column. Passage of the sample through the prefiltration column serves to trap and remove fluid components that are not desired in the final separation product. For example, in blood cell separations, "sticky" cells such as monocytes, granulocytes and platelets may be removed from the cell suspension by the prefiltration column. Alternatively, the prefiltration column may be constructed to have an average pore size that is smaller than that found in the separation column. For example, the pore size of the permeable matrix may be selected to remove large tumor cells from the sample prior to the fluid's passage through the separation column. The passage of the fluid sample through the prefiltration column may also serve to break apart aggregates, such as cell aggregates, that may exist in the fluid. Moreover, because the prefiltration column contains materials substantially identical to those of the separation column, those sample components that might nonspecifically bind to the separation column are advantageously caught by the prefiltration column. Thus, the prefiltration column reduces the possibility of fouling the separation column during the separation process, and it reduces the collection of unwanted cells or fluid components in the final separation product.

Referring to FIG. 2, a preferred embodiment of separation device 25 is depicted. Sample container 81 is connected to an optional suspension filter 35. The suspension filter may be used to remove unwanted particulate components from the fluid sample and is selected to have a pore size sufficient to remove particulates above a certain size. For example, the suspension filter may be a Pail Filter (Pall SQ40S; Pall Biomedical, Inc., Puerto Rico) having a pore size selected to remove particulates larger than 40 μm, such as cell clots and clumps in hematopoietic cell samples. The suspension filter is connected by fluid pathway two 12 to inlet port 32 of prefiltration column 30.

Outlet port 34 of the prefiltration column 30 is connected by fluid pathway five 15 to inlet port 42 of separation column 40 to which the magnetic field will be applied in the course of the separation process. Outlet port 44 of the separation column is connected by fluid pathway eight 18 to distribution channel 88 which leads to product collection container 83, final wash waste container 84 and unlabeled sample container 85. Separate fluid pathways nine 19, ten 20, and eleven 21 lead to these containers, respectively.

This separation device further includes a wash or buffer container 80 and an initial wash waste container 82, which are connected by fluid pathways one 16 and three 17, respectively, to fluid pathway two 12. Buffer container 80 is also connected via wash or buffer line 90 (fluid pathway six) to distribution channel 88. The buffer line is further connected to fluid pathway five 15 by means of fluid pathway four 14. The fluid pathways, containers, filters and columns may be coupled to one another by means of any suitable means such as standard spikes, Luer locks, male-female connectors, T-connectors, Y-connectors and 4-way connectors or other fittings as are commonly used in intravenous solution delivery sets.

Fluid flow through the fluid circuitry of the separation device can be controlled by means of valves placed within the fluid pathway(s). Fluid pathways one through eleven are associated with corresponding valves one through eleven (1–11). The valves may be inside the pathways themselves or may be external to the pathways. The fluid flow may also be controlled by a pump. For example, when the fluid pathways are made of a flexible material, such as flexible tubing, suitable valves for the control of fluid transport include pinch valves. The pinch valves close the fluid pathway by depressing the walls of the tubing against one another. It will be appreciated by those skilled in the art that such pinch valves will be selected to accommodate the size of the tubing chosen for use as a fluid pathway. In addition, the compression force of the pinch valve will be selected to achieve the compression of the chosen tubing and thereby effect the closure of the fluid pathway. The valve specifications, therefore, will be matched to the softness or hardness (durometer) specifications of the selected tubing.

The most preferred embodiment of the separation device further includes recirculation loop 92 (fluid pathway seven) such that fluid that has already passed through separation column 40 may be recirculated through the separation column. Typically, a pump 64 will be connected to the recirculation loop to facilitate the recycling of fluid through the separation column as well as control the flow through the column. It will be appreciated by those skilled in the art that a variety of pumps may be used. An exemplary pump is a peristaltic pump that can control the passage of fluid through the recirculation loop in either direction and at variable speeds. The separation device having a recirculation loop allows sequential separations on one column, by a process of binding and elution, followed by a second binding and elution. Sequential separations provide improved purity in the final target population.

FIG. 2 schematically depicts a preferred embodiment of a separation device. It will be appreciated, however, that a separation process may be accomplished using the basic system components, i.e. the improved magnetic separator and collection containers.

It will be appreciated by those skilled in the art that the recirculation means and fluid flow pathways of the present invention are also suitable for use in alternate separation systems. For example, the recirculation means may be advantageously used in a system wherein the separation means involves centrifugal techniques, absorption columns or chemical means as alternatives to the magnetic or electromagnetic separation means.

In an exemplary cell separation process, the fluid pathways and columns are primed by allowing a wash liquid to flow through all of the fluid pathways and columns, preferably at varying flow speeds and pressures. The wash liquid may contain materials such as a physiologically acceptable protein, such as human serum albumin (HSA), which inhibits cells from adhering to the interior surfaces of plastic device components. The wash liquid may also contain small quantities of physiologically acceptable surfactants or detergents, to improve the wetting of the interior surfaces.

It is found that large air bubbles in the fluid pathways are detrimental to the recovery of viable cells. Methods of removing air bubbles from fluid pathways are known in the art, and may be employed for this purpose. A method of particular interest exploits the observation that a permeable frit such as those used in the cap layer and/or base layer will not allow passage of air bubbles at fluid flow rates of less than about 400 ml/minute. A column may be cleared of air bubbles by circulating wash liquid through a recirculation loop at flow speeds of less than about 400 ml/minute. The air bubbles then accumulate outside of the column at the base and/or cap layers. The direction of flow is then reversed, and the bubbles are washed out of the system into a suitable waste bag. Preferably, the sequence is repeated to ensure the removal of all bubbles. The existing bubbles may be intentionally enlarged by the generation of negative pressure.

In such an exemplary process, magnetically-conjugated antibodies may be used to specifically target the desired cells in a mixed cell population. The magnetic reagent is incubated with the mixed cell population, then unbound particles are washed away by any convenient means, e.g. centrifugation, etc. When cell sterility is desired, the antibody incubations and washes may be performed in a closed container process, where the antibodies and wash liquids are added to a sterile container by means of a sterile syringe or similar device. In this way, contamination of the desired cells by air-borne microorganisms is minimized. In such a closed system, particularly where the container is a flexible bag, the mixing of cells and antibody may be improved by injecting a small amount of sterile air, at a ratio of from about 0.5 to 2 of air to liquid, into the container.

The incubated cell suspension, now containing magnetically labeled target cells, is passed through the separation device. The system transports the cells through a magnetic separator which is positioned within or is adjacent to a magnetic field. The source of the magnetic field may be a permanent magnet or an electromagnet. The separation column is preferably constructed to include a ferromagnetic matrix of stacked ferromagnetic spheres, as described above. Optionally, the sample is passed through a prefiltration column, also constructed as described above, prior to passage through the separation column. If the separation column contains a matrix comprised of other than ferromagnetic spheres, then the sample may be first passed through a prefiltration column that is substantially identical to that separation column.

The magnetically labeled cells accumulate in the separation column in response to the magnetic field. The non-labeled cells and other suspension components pass through the separation column and into an unlabeled sample container and/or waste container. The labeled or purified cells may then be eluted from the separation column by either removing the separation column from the magnetic field or removing the magnetic field from the separation column. A wash solution, such as a buffered liquid, is passed through the separation column to wash the labeled cells from the separation column and into a product collection container. The collection container may be used for further processing of the target cells or cryopreservation of the target cells.

In preferred embodiments, the separation column is a high gradient magnetic separation column constructed from ferromagnetic spheres, as described above. The containers referred to herein are typically plastic bags, such as those used for the storage and delivery of intravenous fluids, but any suitable containers can be used. The containers will be selected for their necessary storage or collection volume, their capacity for sterilization and their ability to be used in a closed system, i.e. a separation system from which substantially all of the air can be removed prior to use.

In another preferred embodiment, the magnetically labeled cells are recirculated through the separation column to enhance the selection of the target cells and the removal of unwanted cells or other suspension components. Some preferred embodiments also include the use of a prefiltration column. The prefiltration column, however, is not subjected to a magnetic field. Instead, the preliminary passage of the cell suspension through the prefiltration column results in the capture of suspension components or materials that otherwise might nonspecifically bind to the separation column. Such nonspecific binding may cause the blockage or fouling of the separation column, which could in turn inhibit or reduce the separation and collection of the labeled cell population.

The fluid pathways, collection containers, suspension filter, prefiltration column and separation column, may be constructed, interconnected and supplied as a disposable separation device. The target cells are preferably collected in a sterile blood transfer container from which the cells can be transplanted to the patient or in which the cells can be stored or subjected to further processing. The complete cell separation device may be prepackaged in suitable containers. The prepackaged device can be sterilized and provided ready for use in the improved magnetic separation process of the present invention. The reagents necessary for the desired separation process may also be provided in kit form. For example, a conjugate specific for the target cell population or other analyte may be provided separately from, or with the device. The kit may also include wash solutions, for example standard sterile saline solution, and/or other buffered liquids, such as phosphate buffered saline, 1 mM EDTA and 0.5% human serum albumin. These reagents or other solutions can be provided in containers such as plastic bags that can be connected to the appropriate fluid passages of the cell separation device.

The improved separation system of the present invention may be totally automated. In the automated system, a computer controls the flow of fluids through the fluid circuitry and separation column, controls the magnetic field strength or placement of the magnet and/or separation column to provide for the retention and release of the magnetically labeled target cells or analyte, and directs the final collection products into appropriate containers.

One embodiment of an automated cell separation instrument, as depicted in FIG. 3, includes mechanical, electromechanical and magnetic components. The mechanical components may include: an instrument outer shell or housing 15; adjustable container holder 21; peristaltic pump 64; prefiltration column holder 32, and separation column holder 42. The electromechanical components may include: solenoid pinch valves 1–11; an internal motor (not shown) to drive peristaltic pump 64; an internal motor 100 to move separation column holder 42 (and thereby move the separation column 40) into or out of the magnetic field, or to move the magnet 50; and a bubble detector (ultrasonic sensor) 65, which is used to detect the presence of fluid in the fluid circuitry. The magnetic means may include permanent and electromagnets. It will be appreciated that these individual components may be selected from a number of readily available alternates and may be combined in a variety of configurations without departing from the general description of the improved magnetic separation system of the present invention.

In a preferred embodiment of the separation device, the fluid pathways, solution and collection containers, suspension filter, prefiltration column, separation column and connectors are provided as a preassembled disposable component to the separation system. The separation device is mounted on the separation instrument for the performance of the separation process. Upon completion of the separation process the product collection container may be removed, and the remaining separation device components are disposed.

Preferably, an onboard microprocessor (not shown) controls all of the electromechanical components of the instrument, and software directs the system to perform the appropriate operations in a standard sequence. A video display 62 and operator keypad 60 allow the operator to monitor automatic system operation and to control instrument operation in a manual mode. A printer (not shown) may be connected to the microprocessor for printing process information, labels, etc.

FIG. 3 depicts a separation instrument and mounted separation device. In this embodiment, the separation device is mounted or installed upon the instrument by positioning the tubing of the fluid pathways in their respective external pinch valves 1–11, as described above. Prefiltration column 30 is placed within prefiltration column holder 32. Separation column 40 is placed within separation column holder 42 which is moved relative to magnet 50 by means of retractable arm 44. Adjustable clamp 20 is used to secure hanger arm 21 in a raised position. There are mounts or pegs 22 on the hanger arm on which to place initial wash waste container 82 and buffer and sample containers (not shown) as appropriate. The apparatus may further include storage compartment 70 to separate the final waste container and unlabeled sample container from the product collection container (not shown).

The following examples are offered by way of illustration and not by way of limitation.

EXAMPLES

Example 1

Separation Column/Prefiltration Column

With reference to FIG. 1, a cylindrical housing 4 of nonmagnetic material is selected having a diameter of 20 mm and a total volume of about 14 ml. A first porous frit (polypropylene) is placed in the base of the housing thereby forming base layer 10. The base layer has an average pore size of approximately 100 µm. Ferromagnetic iron spheres are added to the chamber. The spheres have an average diameter of about 0.2 to 0.5 mm, and approximately 60 grams (55 to 65 grams) of the spheres are placed in the container. To avoid overfilling of the chamber, a 0.12 gram tolerance is preferable. The use of spheres having substantially uniform diameters allows the spheres to assume a symmetrical configuration as depicted in FIG. 1 wherein the spheres are stacked in closely interconnected layers. The housing is then vibrated for approximately five seconds to settle the spheres into a uniform matrix 6. A second porous frit or cap layer 8 is placed over the settled spheres and may be pressed into the chamber to further compress and/or hold the spheres in a stacked matrix configuration or lattice-like structure. Upper portion 16 of the separation column is then attached to the top of the housing. The area around inlet port 12 and outlet port 14 may be shaped to facilitate the secure connection of the column to a fluid pathway such as plastic tubing. Such a column, may further include stops 18 which will inhibit the tubing from passing beyond a certain point on the column. The ports may also be formed to include any suitable connecting means such as spikes, luer locks, male-female connectors, etc.

The matrix may be coated as described above. Once the coated matrix has been allowed to dry, the separation column is further treated with about 5 ml of 1% polyvidone, or other suitable hydrophilic material. Excess polyvidone is allowed to pass through outlet port 12, and the separation column is dried.

Example 2

Cell Separation Process

The following cell separation process is exemplified by the separation device of FIG. 2.

Background

In determinations for optimal flow rates, it was found that most of the desired result of a sequence, e.g. washing, eluting, etc. occurs in a short period of time, with longer flow cycles providing little additional benefits. In order to maximize performance, several short cycles are executed in place of one long cycle. This provides improved performance with no net gain in time or volume pumped. In this way, the loss of cells, the physical impact on cells during elution, and the residual contamination are all minimized.

Priming of the separation device

The first phase of the cell separation process involves the filling or priming of the fluid pathways, the suspension filter, and the, prefiltration and separation columns. During the priming process, the magnetic field is typically not applied to the separation column. The priming of the device serves to remove air from the separation system as well as wash the hydrophilic coating (e.g. PVP) from the prefiltration and separation columns. Flow is induced by gravity in some steps and with a pump in others.

The fluid pathways and column are cleared of air bubbles by circulating wash liquid through a recirculation loop at flow speeds of less than about 400 ml/minute. Several cycles at different flowrates are used. The different flowrates induce different flow characteristics through the separation device, as well as negative pressures, both of which aid in dislodging bubbles from the tubing and column. The air bubbles then accumulate outside of the column at the base and/or cap layers. The direction of flow is then reversed, and the bubbles are washed out of the system into a suitable waste bag. The sequence is repeated for 6 cycles of approximately 5 seconds each to ensure the removal of all bubbles. A cycle of about 4 seconds provides for the collection of about 90% of the bubbles. Each successive cycle removes approximately 90% of the previous balance.

Valves 6 and 10 are opened to allow a buffer or other wash solution to flow from the buffer container 80 and pass through the buffer line 90 to the final waste container 84. Valve 10 is closed, and valves 8, 5 and 3 are opened to prime separation column 40 and prefiltration column 30, thereby removing air bubbles and washing the hydrophilic coating from the columns. The waste and bubbles are transported to the initial wash waste container 82. The pump 64 may be activated to facilitate the transport of the wash liquid through the designated pathway rather than using gravity to induce flow through the system. Valve 10 is reopened to allow further gravity drainage of bubbles to the final waste container 84, and the valves are closed. The wash liquid may contain materials such as human serum albumin, which inhibits cells from adhering to the interior surfaces of plastic device components.

Valves 4, 7, 8 and 10 are then opened to prime recirculation loop 92. The pump is activated to circulate buffer through separation column 40 in both clockwise and counterclockwise directions via the recirculation loop. This recirculation process is repeated for the passage of the buffer through both ends of the separation column to sequentially collect and remove remaining air bubbles from the porous matrix and other void spaces of the separation column and to thoroughly wet the interior of the separation column. The recirculation process also serves to further rinse any hydrophilic coating from the separation column. The valves are then closed.

Valves 1, 2 and 3 are opened to allow priming of the suspension filter 35. The valves are then closed. Valves 6, 8, 5 and 2 are then opened to allow passage of the buffer up to the sample container 81. All valves are then closed. In an automated system, ultrasonic sensor 65 is situated next to fluid pathway two 12. If any air bubbles enter the system from the sample container, the interrupted fluid flow in the pathway is detected, and the instrument automatically switches to wash mode. All valves are closed until the operator can remove the air bubble.

First Collection of Magnetically Labeled Cells

In the collection phase, a magnet is positioned relative to separation column 40 such that a magnetic field is applied to the separation column. Relative positioning may entail moving a magnet around or adjacent to the separation column, or moving the separation column into the magnetic field. In one embodiment of the present invention where a permanent magnet is used to provide the magnetic field, it is advantageous to maintain the magnet in a fixed position as it is a relatively heavy component of the separation system. Thus, the separation column is mounted in or attached to an arm means (not shown) which serves to retract the separation column into the magnetic field for the separation phase and then displace the separation column from the magnetic field for the elution and/or wash phases.

In this example, the separation column 40 is retracted into the magnetic field of a permanent magnet. Valves 1, 5, 8 and 11 are opened to draw air bubbles from the bottom of prefiltration column 30 and separation column 40, and the valves are then closed. Valves 6, 8 and 4 are opened to draw any air bubbles to buffer line 90. Valves 8 and 4 are closed, and valve 10 is opened to allow the gravity drain of the buffer to final waste container 84. All valves are then closed.

Valves 2, 5, 8 and 11 are opened to initiate the flow of sample from sample container 81 and its sequential transport through suspension filter 35, prefiltration column 30 and separation column 40. The target cells or analyte which have been bound by a magnetic reagent are retained in the separation column in the presence of the magnetic field. Unlabeled cells and/or other fluid components pass through the system and are collected in unlabeled sample container 85. This process continues until the sample container empties and an air bubble is detected in fluid pathway two 12. The valves are then closed.

First Wash of the Separation Column

A first wash of the fluid circuit is accomplished by opening valves 1, 5, 8 and 11 to allow the passage of buffer through the prefiltration and separation columns. The pathway is washed and empties into unlabeled sample container 85. Valves 1 and 5 are closed, and valves 7 and 4 are opened to allow a gravity wash of recirculation loop 92. The valves are then closed. The unlabeled cell container is advantageously connected to the fluid circuit on a separate fluid pathway so that the unlabeled cells are not destroyed or contaminated during the separation process.

Valves 4, 8 and 10 are opened to allow the buffer to rinse the separation column to final waste container 84. The valves are then closed.

Valves 6, 5, 8 and 3 are opened to transport fresh buffer back through the system, including the prefiltration column 30. This is a safety procedure to remove residual cells on top of the connectors. The valves are then closed. Valves 4, 8 and 10 are reopened to allow the buffer to rinse the separation column 40 to final waste container 84. The valves are then closed.

Valve 7 is opened, and pump 64 is activated to backwash the separation column 40 with buffer entering the separation column by means of outlet port 44. Valves 4, 8 and 10 are then opened to allow the gravity rinse of recirculation loop 92 into final waste container 84. Valve 7 is closed, and buffer washes the separation column to the final waste container. All valves are then closed. This sequence is repeated 3 times using short cycles, to improve the effectiveness and allow the use of lower flowrates.

A pump means is advantageously used in this and other steps in the separation process. Not only can a pump change the direction of fluid flow, or fluid circulation in conjunction with the recirculation loop, but it may also be operated at different speeds. The different speeds allow the fluid to be pumped at variable rates and to be transported through the system without depending upon gravity alone. For example, a wash of the separation column or fluid pathways may be performed at an increased speed to better clear nonspecifically bound materials from the system. In addition, the pump in conjunction with the recirculation loop allows for the agitation of fluid through the system. Such agitation can be also be used to help wash wanted or unwanted sample materials through the system.

First Elution of Separated Cells from the Separation Column

Valves 6 and 11 are opened to rinse distribution channel 88. The valves are all closed, and the magnet is turned off or the separation column 40 is removed therefrom. Valve 7 is opened, and buffer is transported through separation column thereby washing the separated magnetically-labeled cells from the separation column. Pump 64 may be used to facilitate the transport of the buffer back and forth through the separation column to repeatedly backwash and wash the labeled cells from the separation column. Valve 7 is then closed.

It is possible that some labeled or unlabeled cells may become physically trapped or wedged inside the porous matrix or other void spaces of the separation column as the sample is passed down through that chamber. By backwashing the separation column, (i.e., transporting the wash solution up through separation column outlet port 44, through the matrix and out inlet port 42) the recovery of separated cells is enhanced by pushing any entrapped cells back through the chamber in the direction from which they entered. This is clearly preferable to forcing the cells through the matrix in the elution phase and thereby possibly rupturing the cells.

Re-collection of Magnetically Labeled Cells

In a preferred magnetic separation process, a second collection or re-collection of the magnetically labeled cells is performed. The magnet is turned on or the separation column 40 is again placed within the magnetic field. Valve 7 is opened, and the fluid containing the labeled cells is recirculated through the separation column via recirculation loop 92. Preferably, the fluid is circulated counterclockwise. This results in the entry of the labeled cells into the separation column via separation column outlet port 44. This in turn results in the re-collection of the majority of the magnetically labeled cells in the lower portion of the separation chamber from which the cells may be readily eluted. Valves 6, 8, 5 and 3 may be opened to clear the lower fittings or connectors of any labeled cells for re-collection in the separation column. The valves are then closed. Valve 7 may also be reopened to clear the recirculation loop of any labeled cells for re-collection in the separation column.

Second Wash of the Separation Column

A second wash of separation column 40 may be performed. The fluid is circulated through recirculation loop 92 to wash the lower portion of the separation column. Valves 4, 8 and 10 are opened to allow for the gravity rinse of the recirculation loop and passage of the rinse buffer to final waste container 84. The valves are then closed. This sequence of steps may be repeated. Valves 6 and 11 are opened to clear distribution channel 88, and then the valves are closed. This sequence is repeated 3 times using short cycles.

Final Elution of Labeled Cells from the Separation Column

The magnet is again turned off or removed. Valves 4, 8 and 9 are opened, thereby allowing buffer to wash the magnetically labeled cells from the bottom of separation column 40 into product collection container 83. Valve 7 may be opened and pump 64 may be activated to backwash cells from the separation column. The pump is then stopped to allow the continued wash of the separation column to the product collection container. This step may be repeated. A final collection of labeled cells is accomplished by gravity drainage of the recirculation loop 92. All valves are then closed. The elution recovers at least about 90% of the bound cells. A second elution may be performed to collect the residual bound cells, using the parameters as described above, but including the passage of wash solution through the recirculation loop to more vigorously wash the column. Such a two-step process allows the majority of target cells to escape the more vigorous elution process.

The product collection container 83 now holds the labeled cells and can be removed from the separation device. The separation process also results in the collection of unlabeled cells and other uncontaminated sample components in an unlabeled sample container 85. If a mistake is made in the separation process, the sample may be recovered in the unlabeled sample container and the procedure may be restarted. In addition, the recovery of cells or other components in the unlabeled sample container allows the use of the recovered materials in further separation procedures or other processes. Optionally the cells are directly eluted into a bag suitable for freezing or other storage. In a cell separation process, for example, 10–20% of the target cell population may pass to the unlabeled cell container, but the uncontaminated contents of that container may be reprocessed through the separation device. Preferably, less than 20% of the target cell population will pass to the unlabeled sample container during a separation process.

The enrichment factor is the number of unlabeled cells that pass through the process per unlabeled cells that are non-specifically retained by the device. Usually the separation/recollection process described above will give an enrichment factor for large scale preparative processes of at least about 1000, more usually at least about 3,000, and preferably at least about 5,000. Large scale processes will usually result in the collection of at least about $10^7$ target cells, more usually at least about $10^8$ target cells. A sample of peripheral blood having a starting population of 0.1% CD34 positive cells will result in the collection of a target cell population of approximately 70–90% purity, corresponding to an enrichment factor of 3000 to 10,000. Similar results may be obtained where the starting sample material is prepared from buffy coat (generally containing about 0.1% progenitor cells) or a leukapheresis product from patients treated with an agent to mobilize $CD34^+$ cells (generally containing about 2.0% progenitor cells).

Example 3

Hematopoietic Progenitor Cell Collection

Sample Preparation

In an exemplary cell separation process, human blood cells provide the sample cell population. Mixed cell populations such as peripheral blood, bone marrow, blood from the umbilical cord or placenta, or fetal blood may be used, and are harvested by standard techniques. Standard techniques are also used in the initial preparation of the cell sample (e.g. Ficoll-Hypaque density separation, centrifugation and supernatant removal, etc.). Typical sample preparation procedures will reduce the volume of the sample, thereby concentrating the target cells and reducing the amount of fluid that must be used in the separation system. By preconcentrating the sample, less antibody is needed for the separation process and binding occurs more rapidly. The preferred starting material is a leukapheresis product from patients treated with an agent to mobilize $CD34^+$ cells.

Magnetic Conjugate Incubation

The magnetic label is an iron/polysaccharide particle conjugated to a murine monoclonal antibody that specifically binds CD34, a surface antigen found on hematopoietic stem and progenitor cells. In a sterile bag, the cell suspension is spun down at 500× g for 10 minutes. Using a vented spike adapter, the plasma supernatant is withdrawn from the bag, being careful not to remove any white cells. From a starting volume of 600 ml, approximately 95 g of sample is left in the bag. The cell pellet is resuspended in the remaining fluid. Using a sterile syringe and needle, the conjugated monoclonal antibody (10 ml of magnetic reagent containing 200 μg of antibody) is injected into the bag through a coupler. Sterile air (120 cc) is injected into the bag to aid in proper mixing. The bag is sealed and rocked at room temperature for 30 minutes. Normal saline +0.5% HSA (500 ml) is added to the sample bag, and mixed thoroughly. The sample is centrifuged at 500× g for 10 minutes. Supernatant (500 grams) is removed from the bag through the coupler. The cell pellet is resuspended in the remaining fluid. The wash steps are repeated. The resulting concentrated cell population is then resuspended and is ready for cell separation.

Cell Separation

The stem cell separation procedure takes approximately thirty minutes using an automated system as depicted in FIG. 3. The operator first loads the separation device (tubing and column set) onto the instrument and connects the bag containing the wash liquid or buffer and the bag containing the antibody-treated cells (approximately five minutes) to the device. The automated system then washes and primes the fluid circuitry (approximately five minutes) and initiates the separation process (approximately twenty minutes) as described above. The rest of the run is performed automatically without operator intervention. The instrument will signal that the run is done.

Magnetically labeled cells (e.g. CD34-positive cells) are retained within the separation column by means of magnetic force. The column is then washed and the eluate collected in a discard container. Upon removal of the magnet, the column is again washed and the selected antibody/cell complex is collected in a separate container. The purified CD34-positive cells (or other specific cell population) are then ready for use. A hand sealer may be used to close off the tubing between the stem cell collection container and the rest of the separation device by creating seal points above and below a connecting Luer lock. The stem cell collection container may then be removed.

The collected cells may be cryopreserved or used immediately. The cells may also be subjecting to further processing such as ex vivo expansion to enhance the number of stem/progenitor cells to be transplanted. In the absence of an additional removal procedure, the cell suspension will contain a very small quantity of the antibody reagent which remains attached to the cells (>99% of the antibody reagent is unbound and this is removed by a cell wash prior to cell separation).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A separation system, comprising:
   (a) a separation device comprising:
      (i) a separation column that connects by a first fluid pathway to a sample container wherein said separation column comprises a non-magnetic housing having an inlet port connected to said first fluid pathway, an outlet port, and defining a separation chamber disposed between said inlet port and said outlet port, said separation chamber having a diameter to length ratio of at least 0.2 to 1, and a fluid permeable matrix of ferromagnetic spheres disposed within said chamber;
      (ii) a distribution channel connected by a second fluid pathway to the outlet port of said separation chamber, wherein said distribution channel leads to
      (iii) a product collection container by a third fluid pathway,
      (iv) a wash waste container by a fourth fluid pathway, and
      (v) an unlabeled sample container by a fifth fluid pathway; and
      (vi) a buffer container connected to said first fluid pathway by a sixth fluid pathway, to said second fluid pathway by a seventh fluid pathway and to said distribution channel by an eight fluid pathway; and
   (b) a separation instrument, comprising a housing including:
      (i) a sample container holder;
      (ii) one or more valve means positioned so as to control fluid flow through one or more of said fluid pathways;
      (iii) a pump means to control the flow of fluid through said fluid pathways;
      (iv) a separation column holder; and
      (v) a magnetic field generating means for applying a magnetic field to said matrix of ferromagnetic spheres;
   wherein said separation device may be installed upon said separation instrument by positioning said fluid pathways on said valve means and said separation column on said separation column holder for the performance of a separation process and upon completion of the separation process the separation device may be removed.

2. The separation system in accordance with claim 1, wherein said separation device further comprises a recirculation loop connecting said first fluid pathway and said second fluid pathway such that sample which has passed through said separation column may be redirected to said separation column.

3. The separation system in accordance with claim 2, wherein said separation instrument is an automated separation instrument, further comprising means for automatically controlling said pump means connected to said recirculation loop.

4. The separation system in accordance with claim 3, further comprising a motor means to move said separation column holder, and thereby move the separation column, into or out of the magnetic field.

5. The separation system in accordance with claim 4, further comprising an ultrasonic sensor to detect the presence of fluid in said first fluid pathway.

6. The separation system in accordance with claim 4, further comprising:
   (a) a microprocessor means to control said valves, said pump means and said motor, and thereby direct said instrument to perform the appropriate separation operations in a desired sequence; and
   (b) a video display to allow an operator to monitor automatic system operation.

7. The separation system in accordance with claim 6, further comprising an operator keypad to allow the operator to further operate the instrument in a manual mode.

8. The separation system in accordance with claim 3, further comprising a motor means to move said magnetic field generating means relative to said separation column, and thereby remove the magnetic field from said separation column.

* * * * *